(12) United States Patent
Stump et al.

(10) Patent No.: US 6,221,844 B1
(45) Date of Patent: Apr. 24, 2001

(54) ANTIFUNGAL PEPTIDES FROM SCLERODERMA TEXENSE

(75) Inventors: Heike Stump, Karben; Wilhelm Stahl, Idstein; Joachim Wink, Rödermark; Astrid Markus, Liederbach; Herbert Kogler, Glashütten; Jürgen Backhaus, Edingen, all of (DE)

(73) Assignee: Aventis Pharma Deutschland GmbH, Frankurt am Main (DE)

( * ) Notice: Subject to any disclaimer, the term of this patent is extended or adjusted under 35 U.S.C. 154(b) by 0 days.

(21) Appl. No.: 09/155,603

(22) PCT Filed: Mar. 25, 1997

(86) PCT No.: PCT/EP97/01507

§ 371 Date: May 18, 1999

§ 102(e) Date: May 18, 1999

(87) PCT Pub. No.: WO97/36921

PCT Pub. Date: Oct. 9, 1997

(30) Foreign Application Priority Data

Apr. 1, 1996 (DE) .............................. 196 12 805

(51) Int. Cl.$^7$ .......................... A61K 38/00; A61K 38/02; C07K 5/00; C07K 7/00; C07K 15/00
(52) U.S. Cl. ................ 514/13; 514/2; 530/300; 530/326
(58) Field of Search .......................... 514/13, 2; 530/300, 530/326

(56) References Cited

FOREIGN PATENT DOCUMENTS

0622375 * 11/1994 (EP) .
9736921 * 10/1997 (WO) .

OTHER PUBLICATIONS

Fujita et al., *Journal of Antibiotics*, vol. 41, No. 6 pp. 814–818, Jun. 1988.*

* cited by examiner

*Primary Examiner*—Avis M. Davenport
(74) *Attorney, Agent, or Firm*—Foley & Lardner

(57) ABSTRACT

The invention relates to novel peptides, namely texenomycins, from Scleroderma texense, a process for their preparation and their use as pharmaceuticals, in particular as antimycotics.

The texenomycins according to the present invention are distinguished in particular by the amino acid sequence I (I)

FB-Pro-Aib-Aib-Aib-Aib-Ala-Ala-Aib-βAla-Leu-Aib-βAla-Ala-Aib-βAla-Ala-Aib-Aib-Aib-Ala-Arg-ol in which
 FS is an oxo fatty acid radical,
 Aib is aminoisobutyric acid and
 Arg-ol=argininol.

14 Claims, No Drawings

SEQUENCE LISTING

```
<160> NUMBER OF SEQ ID NOS: 1

<210> SEQ ID NO 1
<211> LENGTH: 21
<212> TYPE: PRT
<213> ORGANISM: Scleroderma texense
<220> FEATURE:
<221> NAME/KEY: MOD_RES
<222> LOCATION: (2)..(5)
<223> OTHER INFORMATION: Aib
<221> NAME/KEY: MOD_RES
<222> LOCATION: (8)
<223> OTHER INFORMATION: Aib
<221> NAME/KEY: MOD_RES
<222> LOCATION: (9)
<223> OTHER INFORMATION: bAla
<221> NAME/KEY: MOD_RES
<222> LOCATION: (11)
<223> OTHER INFORMATION: Aib
<221> NAME/KEY: MOD_RES
<222> LOCATION: (12)
<223> OTHER INFORMATION: bAla
<221> NAME/KEY: MOD_RES
<222> LOCATION: (14)
<223> OTHER INFORMATION: Aib
<221> NAME/KEY: MOD_RES
<222> LOCATION: (15)
<223> OTHER INFORMATION: bAla
<221> NAME/KEY: MOD_RES
<222> LOCATION: (17)..(19)
<223> OTHER INFORMATION: Aib

<400> SEQUENCE: 1

Pro Xaa Xaa Xaa Xaa Ala Ala Xaa Xaa Leu Xaa Xaa Ala Xaa Xaa Ala
 1               5                  10                  15

Xaa Xaa Xaa Ala Arg
             20
```

ANTIFUNGAL PEPTIDES FROM SCLERODERMA TEXENSE

The invention relates to novel peptides, namely texenomycins, from Scleroderma texense, in particular the peptides texenomycin A and B, a process for their preparation and their use as pharmaceuticals, in particular as antimycotics.

The texenomycins according to the present invention are distinguished in particular by the amino acid sequence I (SEQ ID NO: 1).

FB-Pro-Aib-Aib-Aib-Aib-Ala-Ala-Aib-βAla-Leu-Aib-βAla-Ala-Aib-βAla-Ala-Aib-Aib-Aib-Ala-Arg-ol    (I)

in which
  FS is an oxo fatty acid radical,
  Aib is aminoisobutyric acid and
  Arg-ol=argininol.

The fatty acid radical consists of 3 to 20, preferably of 8 to 15, carbon atoms.

The oxo group of the fatty acid radical is preferably located in the 3-position.

Compounds which correspond to the texenomycins have not been described in the literature to date. Structurally comparable compounds, such as the recently described trichosporins (cf. T. Fujita et al., J. Antibiotics (1988), 41, 814) differ, however, solely by the lower number of Aib radicals and by the amino acid sequence.

The fatty acid radical of the peptides according to the invention particularly preferably has the constitutional formula II

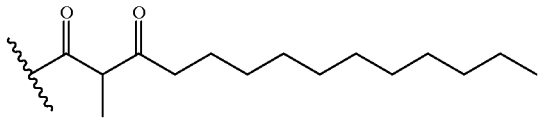
(II)

where the preferred peptides texenomycin A and B differ from one another only by the configuration (R or S configuration) of the carbon atom arranged between the two carbonyl groups or by the spatial arrangement of the methyl group substituting this atom.

The preferred texenomycins A and B are formed by the fungus Scleroderma texense, preferably Scleroderma texense DSM 10601, and are characterized in that they have the empirical formula $C_{97}H_{170}N_{24}O_{23}$ (texenomycin A) or $C97H_{170}N_{24}O_{23}$ (texenomycin B), have a UV maximum at 280 nm (measured in methanol) and have the melting points of 215–216° C. (texenomycin A) or 209° C. (texenomycin B).

The subject of the present invention furthermore includes the processes for the preparation of the compounds mentioned. A process for the preparation of the compounds mentioned comprises culturing the microorganism Scleroderma texense, preferably Scleroderma texense DSM 10601, in an aqueous medium and then isolating and purifying the target compounds.

The microorganism Scleroderma texense DSM 10601 has been deposited on Mar. 20, 1996 in the Deutsche Sammiung von Mikrooganismen und Zellkulturen GmbH [German Collection of Microorganisms and Cell Cultures, (DSMZ)]; Mascheroder Weg 1b, D-38124 Brunswick according to the rules of the Budapest Convention.

Instead of the strain DSM 10601, its mutants and variants can also be employed insofar as they can synthesize peptides of the formula I. Such mutants can be produced in a manner known per se by physical means, for example irradiation, such as with ultraviolet or X-rays, or chemical mutagens, such as, for example, ethyl methanesulfonate (EMS), 2-hydroxy-4-methoxybenzophenone (MOB) or N-methyl-N'-nitro-N-nitrosoguanidine (MNNG).

The present invention accordingly also relates to Scleroderma texense DSM 10601 and its mutants and variants.

The fermentation conditions described below apply to Scleroderma texense and the deposited isolate DSM 10601. The fermentation can be carried out on the laboratory scale (milliliter and liter scale) or on the industrial scale (cubic meter scale).

In a nutrient solution which contains a carbon source and a nitrogen source as well as the customary inorganic salts, S. texense, in particular S. texense DSM 10601, produces the peptides of the formula I.

Suitable preferred carbon sources for aerobic fermentation are assimilable carbohydrates and sugar alcohols, such as glucose, lactose or D-mannitol, and carbohydrate-containing natural products, such as, for example, malt extract. Suitable nitrogen-containing nutrients are: amino acids, peptides and proteins and also their degradation products, such as peptones or tryptones, furthermore meat extracts, ground seeds, for example of corn, wheat, beans, soy or of the cotton plant, distillation residues from alcohol production, meat meals or yeast extracts, but also ammonium salts and nitrates. Inorganic salts which the nutrient solution can contain are, for example, chlorides, carbonates, sulfates or phosphates of the alkali metals or alkaline earth metals, iron, zinc, cobalt and manganese.

The formation of the compound of the formula I using S. texense, preferably DSM 10601, proceeds particularly well in a nutrient solution which contains 0.05 to 5%, preferably 0.1 to 2%, of casein peptone, 0.5 to 7%, preferably 0.1 to 2%, of meat peptone, 0.1 to 5%, preferably 0.5 to 3%, of glucose, and also 0.1 to 5%, preferably 0.5 to 3% of maltose, in each case based on the weight of the total nutrient solution.

Culturing is carried out aerobically, i.e., for example, under submerse conditions with shaking or stirring or in fermenters, if appropriate with introduction of air or oxygen. It is carried out in a temperature range from 15 to 30° C., in particular from 23 to 28° C. The pH is from pH 1 to 7, advantageously from pH 2.5 to 4.5. The fungus is cultured under these conditions over a period of 100 to 300 hours, preferably 120 to 168 hours.

Culturing is advantageously carried out in several stages, i.e. one or more precultures are first prepared in liquid nutrient medium, which are then transferred into the actual production medium, the main culture, for example in the volume ratio 1:10. The preculture is obtained, for example, by transferring mycelium into a nutrient solution and allowing it to grow for approximately 100 to 200 hours, preferably 120 to 168 hours. The mycelium can be obtained, for example, by allowing the strain to grow for 7 to 40 days, preferably 10 to 20 days, on a solid or liquid nutrient medium, for example yeast-malt agar or potato-dextrose agar.

The course of the fermentation can in each case be monitored by means of the pH of the culture or the mycelium volume and also by chromatographic methods, such as, for example, thin-layer chromatography or high-pressure liquid chromatography (HPLC).

The texenomycins can occur both in the mycelium and in the culture filtrate, usually the main amount is found in the cell mass. It is therefore expedient to separate this from the filtrate by filtration or centrifugation. The filtrate is lyophilized and the lyophilizate is extracted with a solvent such as methanol, acetonitrile or 1-butanol. Texenomycins can be extracted from the mycelium in the same manner. The extractions can be carried out over a wide pH range; a range of pH 3.0–7.5 is expedient.

Another method of isolation is solution partition in a manner known per se.

Another method of purification is chromatography on adsorption resins such as, for example, on Diaion® HP-20 (Mitsubishi Casei Corp., Tokyo), on Amberlite® XAD 7 (Rohm and Haas, USA), on Amberchrom® CG (Toso Haas, Philadelphia, USA) or on similar supports. Numerous reversed-phase supports are moreover suitable, e.g. RP-18, such as are generally used in high-pressure liquid chromatography (HPLC). A further possibility of purification for the texenomycins consists in the use of so-called straight-phase supports such as, for example, silica gel or alumina. Many solvents such as, for example, chloroform/methanol/glacial acetic acid mixtures are suitable for elution.

An alternative process for the isolation of the texenomycins is the use of so-called molecular sieves, such as, for example, Fractogel® TSK HW-40, Sephadex® LH-20. It is moreover also possible to obtain the texenomycins from enriched material by crystallization. For example, organic solvents and their mixtures, anhydrous or with addition of water, are suitable for this purpose. Additions of acids, such as, for example, trifluoroacetic acid, sulfuric acid, hydrochloric acid, formic acid or others, can likewise be advantageous.

It was found that the texenomycins inhibit the growth of various human-pathogenic fungi, e.g. *Candida albicans* with an MIC (minimum inhibitory concentration) of 0.24 µg/mL (Tex. A) or 0.49 µg/mL (Tex. B).

The substances according to the invention are suitable for the therapy and prophylaxis of fungal infections.

The present invention therefore also relates to a peptide of the formula I for use as a pharmaceutical, and in particular a pharmaceutical comprising at least one peptide as in formula I and pharmaceutical auxiliaries.

The invention relates in particular to the use of the texenomycins or their derivatives for producing a pharmaceutical for the treatment of fungal infections.

EXAMPLES 1. a) Preparation of mycelium of the producer strain S. texense DSM 10601

100 ml of nutrient solution (20 g of malt extract, 2 g of yeast extract, 10 g of glucose, 0.5 g of $(NH_4)_2HPO_4$ in 1 l of mains water, pH before sterilization 6.0) in a 500 ml sterile Erlenmeyer flask are inoculated with the strain DSM 10601 and incubated for 240 hours at 25° C. and 140 rpm on a rotating shaker. 20 ml of culture liquid are then uniformly distributed in a sterile 500 ml Erlenmeyer flask containing the nutrient medium [potato infusion 4.0 g/l (infusion of 200 g of potatoes in 1000 ml of $H_2O$), 20.0 g of D-glucose, pH before sterilization 5.6], to which 15 g of agar/l have additionally been added for solidification, and decanted. The cultures are incubated at 25° C. for 10 to 21 days.

The mycelium resulting after this time in a flask is removed using a sterile inoculation needle, immediately reused or stored in water at 4° C.

1. b) Preparation of a culture or of a preculture of the producer strain in the Erlenmeyer flask A sterile 500 ml Erlenmeyer flask containing 100 ml of the nutrient solution described under a) is inoculated with a culture grown in a slant tube or a piece of mycelium 1 ccm in size and incubated on a shaker at 140 rpm and 25° C. The maximum production of the compound of the formula I is achieved after about 168 hours. A submerse culture which is 72 hours old (inoculation quantity about 5%) of the same nutrient solution suffices for inoculating 10 and 100 l fermenters.

2. Preparation of the compound of the formula I

A 10 l fermenter is operated under the following conditions:

| | |
|---|---|
| 5 g/l | casein peptone |
| 10 g/l | maltose |
| 5 g/l | meat peptone |
| 10 g/l | glucose |
| pH 6.5 | (before sterilization) |

The pH is adjusted using aqueous 2N NaOH or HCl.

Incubation time: 168 hours

Incubation temperature: 25° C.

Stirrer speed: 200 rpm

Aeration: 5 l of air/min

Foam formation can be suppressed by repeated addition of a few drops of ethanolic polyol solution. The production maximum is achieved after about 96 hours.

3. Isolation of the texenomycins 8 l of the culture solution obtained according to Example 2 are removed by centrifugation and the cell mass is freeze-dried. 35 g of the lyophilizate are washed twice by stirring with 600 ml of methanol each time and in each case filtered off with suction through coarse-pore filter paper. The filtrate is freed of the solvent and lyophilized after addition of water. 8 g of the lyophilizate are digested with methanol and filtered again.

4. Purification of the texenomycins 150 ml of the methanolic solution from Example 3 are chromatographed on Fractogel® TSK HW-40 (column volume 2.5 l) using methanol (flow rate 40 ml/min). The texenomycin A-containing fractions are combined and concentrated in vacuo.

The enriched material is slurried in acetonitrile/methanol, filtered through cellulose filters, diluted to a 30% solvent content with water and chromatographed (column dimensions 250×20 mm, flow rate 23 ml/min) on Merck RP-select B using an acetonitrile-water gradient (0.05% trifluoroacetic acid, 50 to 100 acetonitrile). The texenomycin A-containing fractions are combined, concentrated in vacuo and lyophilized (45 mg of texenomycin A as a white powder). Texenomycin B is obtained analogously from texenomycin B-containing fractions after Fractogel® TSK HW-40.

The structure of the texenomycins obtained was determined by NMR spectroscopy.

5. Antifungal spectrum of action of texenomycin A+B in microdilution tests

| | MIC (µg/ml) | |
|---|---|---|
| Test microorganism | texenomycin A | texenomycin B |
| *Candida albicans* | 0.24 | 0.49 |
| *Aspergillus fumigatus* | 0.24 | 0.49 |
| *Microsporum canis* | 0.49 | 7.81 |
| *Trichophyton mentagrophytes* | 7.81 | 15.6 |
| *Trichophyton rubrum* | 31.25 | 31.25 |

MIC = minimal inhibitory concentration

Antibacterial and antifungal spectrum of action of texenomycin A and B, concentration employed: 1 mg/ml

| Test microorganism | Agar diffusion test [mm inhibition halo] | |
| --- | --- | --- |
| | texenomycin A | texenomycin B |
| *Candida albicans* | 20 | 20 |
| *Saccharomyces cerevisiae* | 19 | 19 |
| *Aspergillus niger* | 17 | 17 |
| Staph. P209 | 15 | 14 |
| *Bacillus subtilis* | 15 | 15 |
| *Escherichia coli* | — | — |
| *Micrococcus luteus* | 13 | 13 |
| *Pseudomonas fluorescens* | — | — |
| *Streptomyces murinus* | trace | 10 | no activity: 7 mm

What is claimed is:

1. A peptide of amino acid sequence I (SEQ ID NO: 1)

FB-Pro-Aib-Aib-Aib-Aib-Ala-Ala-Aib-βAla-Leu-Aib-βAla-Ala-Aib-βAla-Ala-Aib-Aib-Aib-Ala-Arg-ol (I)

in which

FS is an oxo fatty acid radical,

Aib is aminoisobutyric acid and

Arg-ol=argininol.

2. A peptide as claimed in claim 1, wherein the oxo fatty acid radical consists of 3 to 20 carbon atoms.

3. A peptide as claimed in claim 2, wherein the oxo fatty acid radical consists of 8 to 15 carbon atoms.

4. A peptide as claimed in claim 3, wherein the oxo group of the oxo fatty acid radical is found in the 3-position.

5. A peptide as claimed in claim 4, wherein the oxo fatty acid radical has the constitutional formula II

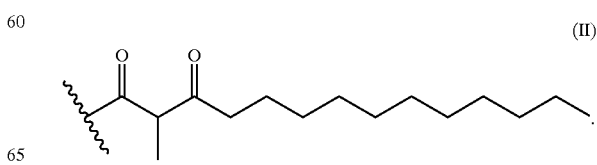

(II)

6. A peptide as claimed in claim 5, wherein the fatty acid radical has an R configuration.

7. A peptide as claimed in claim 5, wherein the fatty acid radical has an S configuration.

8. A process for the preparation of a compound as claimed in claim 1, which comprises culturing Scleroderma texense in an aqueous medium and then isolating and purifying the target compound.

9. The process as claimed in claim 8, wherein Scleroderma texense DSM 10601 is employed.

10. The process as claimed in claim 9, wherein mutants or variants of Scleroderma texense DSM 10601 are employed.

11. A peptide as claimed in claim 1 for use as a pharmaceutical.

12. A pharmaceutical comprising at least one peptide as claimed in claim 1 and pharmaceutical auxiliaries.

13. Scleroderma texense DSM 10601 and its mutants and variants.

14. A method of treating fungal infections, comprising administering the peptide of claim 1 to an individual in need thereof.

* * * * *